(12) United States Patent
Tschudi

(10) Patent No.: US 7,110,577 B1
(45) Date of Patent: *Sep. 19, 2006

(54) METHOD AND APPARATUS FOR MEASURING STRUCTURES IN A FINGERPRINT

(75) Inventor: Jon Tschudi, Oslo (NO)

(73) Assignee: SINTEF, Trondheim (NO)

( * ) Notice: Subject to any disclaimer, the term of this patent is extended or adjusted under 35 U.S.C. 154(b) by 0 days.

This patent is subject to a terminal disclaimer.

(21) Appl. No.: 09/424,210

(22) PCT Filed: Jun. 12, 1998

(86) PCT No.: PCT/NO98/00102

§ 371 (c)(1),
(2), (4) Date: Nov. 22, 1999

(87) PCT Pub. No.: WO98/58342

PCT Pub. Date: Dec. 23, 1998

(30) Foreign Application Priority Data

Jun. 16, 1997 (NO) .................................. 972759

(51) Int. Cl.
G06K 9/00 (2006.01)
(52) U.S. Cl. .................... 382/124; 382/284; 382/323
(58) Field of Classification Search ............... 384/124, 384/125–127, 321, 323; 340/5.53
See application file for complete search history.

(56) References Cited

U.S. PATENT DOCUMENTS

| 3,622,989 A | * | 11/1971 | Dowdy, Sr. ................. 382/126 |
| 4,353,056 A | | 10/1982 | Tsikos |
| 4,394,773 A | | 7/1983 | Ruell |
| 4,429,413 A | | 1/1984 | Edwards |
| 4,784,484 A | | 11/1988 | Jensen |
| 5,325,442 A | | 6/1994 | Knapp |
| 5,503,029 A | | 4/1996 | Tamori |
| 5,559,504 A | | 9/1996 | Itsumi et al. |
| 5,828,773 A | | 10/1998 | Setlak et al. ................. 382/126 |
| 5,841,888 A | | 11/1998 | Setlak et al. ................. 382/124 |
| 5,845,005 A | | 12/1998 | Setlak et al. ................. 382/124 |
| 5,852,670 A | | 12/1998 | Setlak et al. ................. 382/126 |
| 5,862,248 A | * | 1/1999 | Salatino et al. ............. 382/124 |

(Continued)

FOREIGN PATENT DOCUMENTS

EP 735502 10/1996

(Continued)

Primary Examiner—Vikkram Bali
Assistant Examiner—Colin LaRose
(74) Attorney, Agent, or Firm—Rothwell, Figg, Ernst & Manbeck PC

(57) ABSTRACT

Method and apparatus for the measuring of structures in a fingerprint or the like, comprising the measuring of chosen characteristics of the surface of the fingerprint, e.g. by measuring capacitance or resistivity, using a sensor array comprising a plurality of sensors, being positioned in contact with, or close to, a portion of the surface. The characteristics are measured in at least one line of measuring points along an elongated portion of the surface at given intervals of time, the sensor array being an essentially one-dimensional array, moving the surface in relation to the sensor array in a direction perpendicular to the sensor array, so that the measurements are performed at different, or partially overlapping, portions of the surface, combining the measurements of the measured portions of the surface to provide a segmented, two-dimensional representation of said characteristics of the surface.

12 Claims, 3 Drawing Sheets

U.S. PATENT DOCUMENTS

| | | | |
|---|---|---|---|
| 5,864,296 A * | 1/1999 | Upton | 382/124 |
| 5,903,225 A | 5/1999 | Schmitt et al. | 340/825.31 |
| 5,920,640 A | 7/1999 | Salatino et al. | 382/124 |
| 5,940,526 A | 8/1999 | Setlak et al. | 382/124 |
| 5,942,761 A | 8/1999 | Tuli | |
| 5,953,441 A | 9/1999 | Setlak | 382/124 |
| 5,956,415 A | 9/1999 | McCalley et al. | 382/124 |
| 5,963,679 A | 10/1999 | Setlak | 382/312 |
| 6,289,114 B1 | 9/2001 | Mainguet | |

FOREIGN PATENT DOCUMENTS

| | | |
|---|---|---|
| JP | 8154921 | 6/1996 |
| JP | 10003532 | 1/1998 |
| JP | 10222641 | 8/1998 |
| WO | 8606266 | 11/1986 |
| WO | 9600082 | 1/1996 |
| WO | 9632061 | 10/1996 |

* cited by examiner

METHOD AND APPARATUS FOR MEASURING STRUCTURES IN A FINGERPRINT

The invention relates to a method and an apparatus for the measuring of structures in a fingerprint or the like, comprising the measuring of chosen characteristics of the surface of the fingerprint, e.g. capacitance or resistivity, using a sensor array comprising a plurality of sensors, positioned in contact with, or close to, the surface.

Identification by the use of fingerprints has lately come to the fore as a result of the increasing needs for security relating to, for example, credit cards or computer systems as well as the greatly increased availability of pattern recognition algorithms. Some systems for recognition of fingerprints have already been made available on the market. The techniques used to register the fingerprint varies.

Some of the previously known solutions are based upon optical technology using light with one or more wavelengths. These are sensitive to dirt and contamination, both in the fingerprint and on the sensor surface, and thus cleaning is necessary for both.

Another alternative is pressure measurement, such as is described in U.S. Pat. No. 5,559,504, U.S. Pat. No. 5,503,029 and U.S. Pat. No. 4,394,773. This, however, has the disadvantage that the sensor surface becomes sensitive to mechanical wear and damage, as the sensor has to have an at least partially compliant surface.

Temperature sensors have also been suggested, for example in U.S. Pat. No. 4,429,413 and international patent application PCT/NO96/00082.

Since fingerprint sensors may be exposed to long term use in varying and sometimes demanding conditions the sensor needs to have a robust surface and to be as insensitive to pollution in the fingerprint and on the sensor as possible. It must be capable of reading most fingerprints without being disturbed by latent prints from earlier use. In some cases, e.g. in credit cards or computer keyboards, it would also be advantageous if the sensor could be made compact.

In the view of costs there is also a demand for simplicity and minimizing of the number of parts.

It is an object of the present invention to provide a sensor being easy to produce, making them cheap in production, and also relatively small.

In addition to the solutions mentioned above the measuring of capacitance has been tried as a method to measure finger prints. Examples are shown in U.S. Pat. No. 4,353,056 and U.S. Pat. No. 5,325,442. While the ridges of the fingerprint touches the sensor surface the valleys have a small distance to the sensor surface, resulting in a difference in capacitance and/or conduction measured at the different sensors. Humidity may affect the measurements, but if it is even throughout the fingerprint an analysis of the contrast between the measurements can provide a picture of it.

All the solutions mentioned above are based upon two-dimensional sensor arrays with dimensions comparable to the size of the fingerprint. These are expensive and difficult to produce, since they comprise a large number of sensors simultaneously measuring the surface.

EP 735.502 describes the use of a one or two-dimensional array of sensors being moved in relation to the finger print. The described solution is based on the measuring of resistance, and has a limited resolution defined by the minimum sensor dimensions and the distance between the sensors.

The present invention provides a method and an apparatus for the measuring of structures in a fingerprint or the like, for example using one of the techniques described above, characterized as stated in the disclosed claims.

As the surface of the sensor array is small, and contains-few sensors compared to the known solutions, it is inexpensive and relatively simple to make. As the fingerprint to be measured is moved past the sensor array there is no latent fingerprint remaining from the previous user, giving another advantage in relation to the known finger print sensors.

Since the details in the fingerprints are small, it is also difficult to make the sensors of the detector small enough. In a preferred embodiment the apparatus and method according to the invention comprises two or more parallel lines of measuring points, each line of measuring points being shifted in the longitudinal direction with a distance less than the distance between the measuring points, the sensor array comprising two or more parallel lines of equally spaced sensors, preferably shifted in the longitudinal direction of the sensor array. This provides a possibility to measure structures in the fingerprint smaller than the spacing of the sensors. This is not possible with any of the previously known detector systems.

Thus, it is to be understood that the term "essentially one-dimensional array" here refers to an array having a length being much larger than its width, and may comprise more than one line of sensors.

The invention will be described below with reference to the enclosed drawings, which illustrate one possible embodiment of the invention.

FIG. 2b shows a cross section of the situation in FIG. 2a.

Figure 1A:
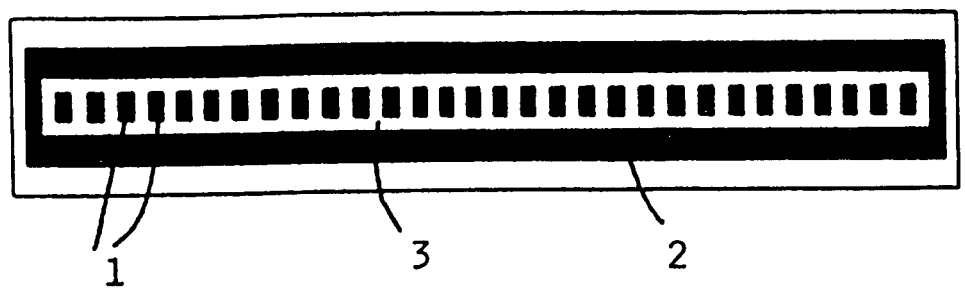
FIGS. 1a and 1b shows a schematic view of two versions of the sensor.

In FIG. 1a a single, linear array of sensors 1 is shown. The sensors may be of different kinds, such as pressure sensors or temperature sensors, but preferably they are electrical conductors providing a possibility to measure conduction, impedance or capacitance of the different parts of the fingerprint. The surface to be measured is moved in a perpendicular direction relative to the line of sensors.

In the preferred embodiment the sensors 1 are electrical conductors separated by an insulating material 3 such as epoxy. In the shown embodiment an electrically conducting material 2 surrounds the sensors which may be used to provide a reference potential. Thus the conduction, impedance or capacitance, through the fingerprint, between each of the sensors 1 and the surrounding reference level may be measured.

The shown embodiment having equally distanced sensors is preferred, but other solutions, e.g. comprising groups of sensors for measuring certain parts of the finger print, are also possible.

Figure 1B:
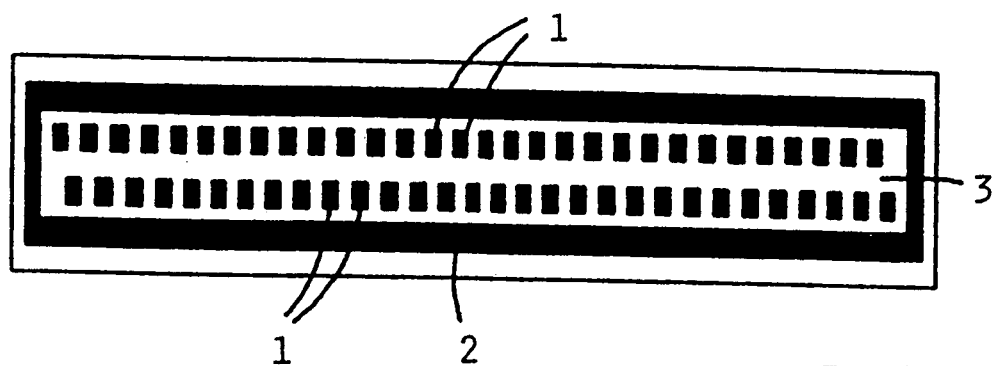

Using one or more sensors positioned at one or more chosen distances from the sensor line will provide a possibility for measuring the velocity of the finger print in relation to the sensor by comparing the signals from the sensor line and the time lapse or spacial shift between the measurements of corresponding structures in the surface. FIG. 1b shows a preferred embodiment of the invention in which the sensor array comprises two lines of sensors 1.

To be able to measure the structures in a fingerprint the array will typically be 10–15 mm long with a resolution of 50 µm. This is difficult or expensive to obtain using a single line of sensors. In FIG. 1b the lines are slightly shifted in relation to each other. When moving a surface across the sensor array the measurements of each of the sensors in the second line will fall between the measured point of the first line, providing the required resolution with a larger distance between the sensors. Three or more lines are possible to improve the resolution even more, but more than five would be impractical because of the distance between the lines and the resulting time lapse between the measurements of the first and the last line. Also, an apparatus using many lines would be sensitive to the direction in which the finger is moved.

Although the lines shown in the drawings comprise equally spaced sensors the shifted, second, third etc. lines may comprise single or groups of sensors, increasing the resolution in certain parts of the finger print, and/or measuring differences in velocity of different parts of the finger print, in case the movements are uneven. Also, the second, third etc. lines may have an angle in relation to the first line of sensors.

When using a sensor array comprising two or more sensor lines, as shown in FIG. 1b, the measurements of the different lines must be combined to provide a signal corresponding to one single line of sensors. To do this the signals from the sensors must be adjusted for the time delay between the signals from the sensors in different lines, and thus the movement of the finger in relation to the sensor array must be known, either by moving the finger or sensor array with a chosen speed, or by measuring the movement of the finger.

Figure 2A:
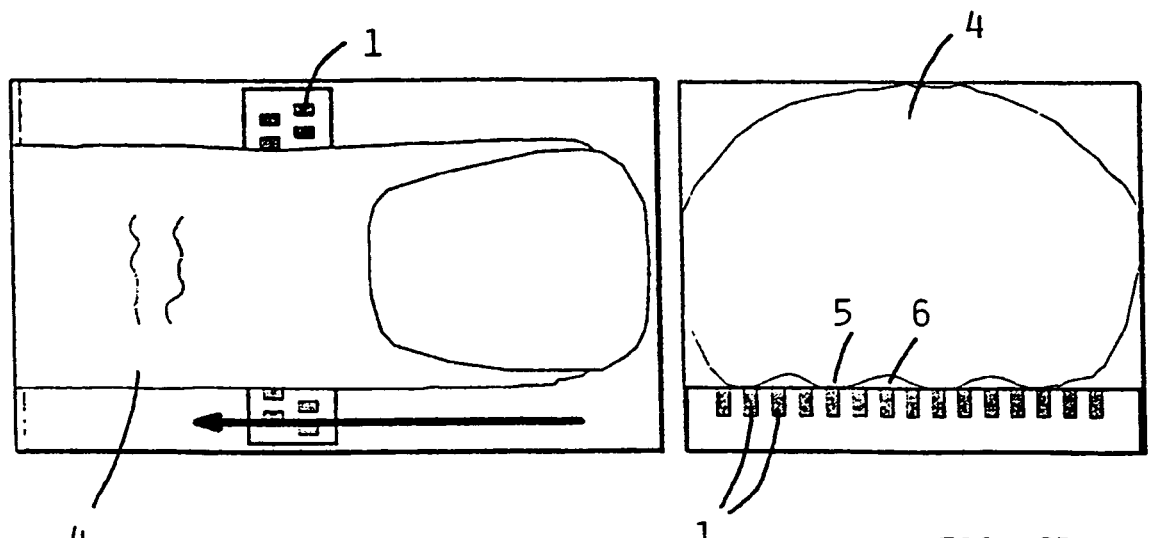
FIG. 2a illustrates the sensor in FIG. 1b in use, as seen from above.

FIG. 2a illustrates how the finger 4 is moved over a sensor array in the direction perpendicular to the array. In order to obtain exact measurements the movement of the finger must be measured. In addition to the abovementioned method comprising the correlation of measurements from different sensors this may be done in many ways, such as providing a rotating cylinder in contact with the finger, so that the rotation of the cylinder may be measured. Another example may be the use of a thin disk on which the finger may be positioned, which is moved together with the finger and is connected to the apparatus so that the velocity of the disk may be measured. Preferably, however, the movement is measured by correlating or comparing the signals from the different sensor lines, and the time lapse or spacial shift between the measurements of corresponding structures in the surface is found. This way more detailed images can be made from the separate images of each line of sensors.

Another method for adjusting for the movement of the finger is to maintain the sampling rate at the sensor array, while adjusting the number of measured lines used in generating the segmented image of the surface, and thus the interval of the measurements according to movement in order to obtain at least one measurement of each portion of the surface. For example, if the fingerprint is moved slowly over the sensor, while the sampling or measuring frequency is high, the redundant data may simply be neglected and the image of the finger print is comprised by each second or third set of data.

Figure 2B:
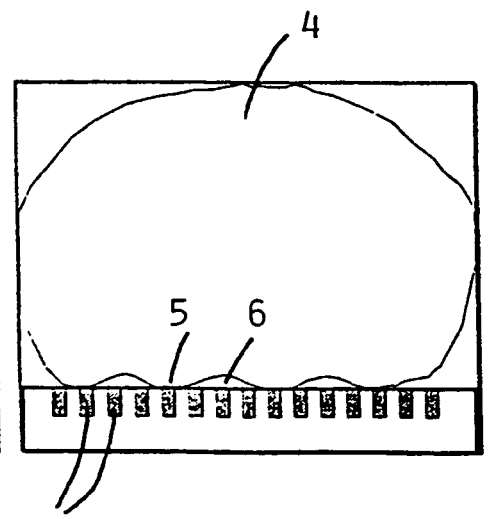

FIG. 2b shows a cross section of the finger 4 placed on the sensors 1, and also shows an exaggerated view of the ridges 5 and valleys 6 in the fingerprint.

Figure 3:
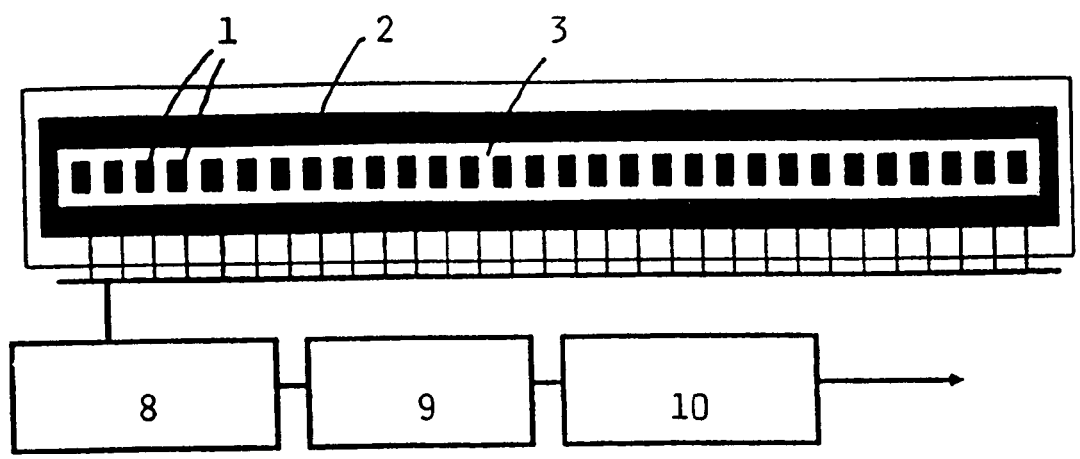
FIG. 3 shows a schematic view of an apparatus according to the invention.

FIG. 3 shows a simplified view of the apparatus according to the invention comprising conductors from the sensors 1 to an amplifier and multiplexer 8. The signal is then digitized in an A/D-converter 9 before the digital signal is sent to a computer 10 comprising any available computer program being able to analyse the signal.

Figure 4:
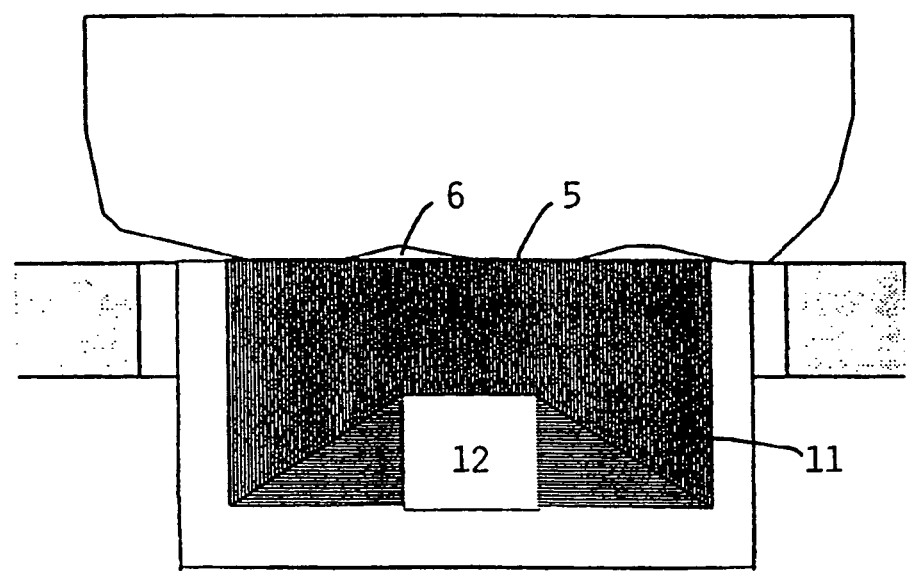
FIG. 4 shows a cross section of an embodiment of the invention.

A cross section of a more realistic embodiment is shown in FIG. 4, in which one end of each of the closely spaced conductors 11 represents the sensors, and the other end of these conductors is connected to a microchip 15. The conductors 11 may be a part of a multi layer printed circuit board moulded in epoxy, producing two or more lines of sensors. Each sensor 1 would be about 35×50 µm. If the sensors in each line are mounted with distance between the centres of 150 µm, the resolution with three shifted lines will be 50 µm.

Figure 5:
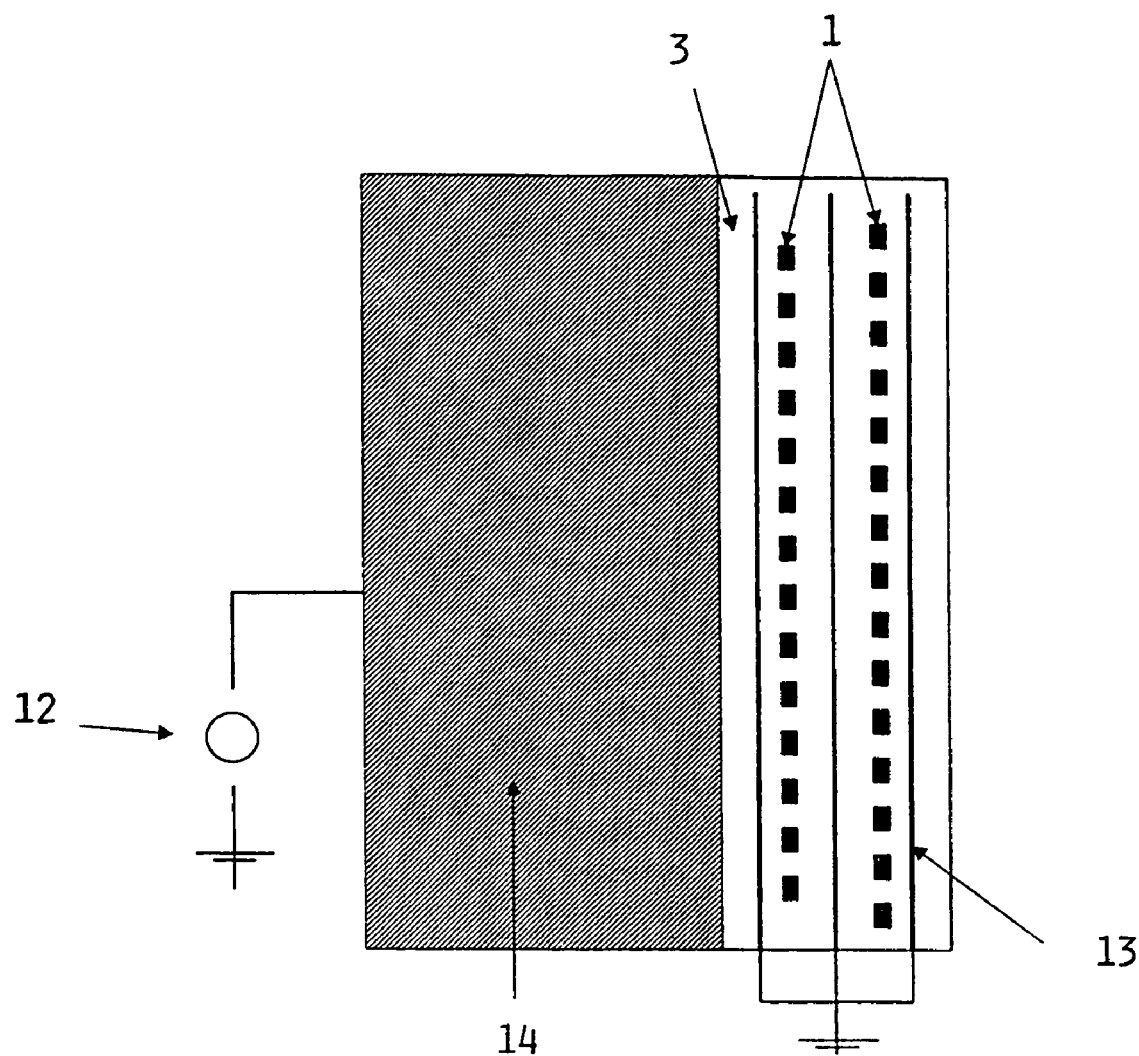
FIG. 5 shows a preferred embodiment of the invention.

FIG. 5 shows an embodiment of the invention where an external time varying, e.g. oscillating or pulsating, voltage 12 is applied to the finger through the conducting area 14 on the side of the sensor area. Planes at a constant voltage 13 are placed close to and parallel to the lines of sensors 1. This reduces cross-talk and noise from external sources, and improves contrast in the image generated from the measurements. This may be implemented by using a multilayer printed circuit board, where one or more of the conducting layers are at a constant voltage. An insulating layer (not shown) preferably covers the conductors 1,11 and shielding planes 13. The conducting area 14 may also be covered by an insulating layer, but this would decrease the signal strength. For better performance the oscillating voltage 12 may be applied to both sides of the sensor surface. The oscillating voltage may, as mentioned above, be a pulse train, or a sinus.

In the one embodiment, a sinus of 100 kHz is applied to the conducting area 14, and each of the conductors 11 is terminated by a resistance, and the signal is amplified and fed to a demodulator, multiplexer and analogue-to-digital converter. One advantage of this embodiment is that there is essentially no signal on the conductors 11 in the sensor area when no finger is present, thus reducing problems with offset voltages varying with time and drift in the electronics.

This solution provides a sensor apparatus being simple to produce using standard techniques, and thus cheap. It is also compact and rugged. If the measured parameter is the resistance the sensors, being the ends of the conductors, will not change their characteristics as they and the surrounding epoxy are worn down. If the capacitance is to be measured a durable, insulating layer is provided on the sensors or conductor ends.

The preferred layout of the sensor also allows the resolution to be better than the distance between the sensors, reducing cross-talk between the sensors.

The method and apparatus according to the invention may of course be utilized in many different ways, and different characteristics may be measured in order to provide a representation of the measured surface, in addition to capacitance and/or conductivity. Optical detectors may be used, and preferably transmitters, so that the reflected image of the fingerprint may be analysed regarding for example contrast and/or colour.

The sensors may, as mentioned above simply be the ends of conductors connected to means for measuring capacitance and/or conductivity, or may be sensors made from semiconducting materials. A preferred semiconducting material when cost is essential would be silicon.

In the embodiment comprising capacitance measurements an insulating layer (not shown) is provided between the conductor ends and the finger print.

Another possible embodiment within the scope of this invention comprises sensor lines of not equally spaced sensors positioned to measure chosen parts of the fingerprint.

The invention claimed is:

1. A method for sensing a fingerprint comprising:
generating a plurality of images of different portions of a fingerprint surface by measuring structural features of the fingerprint surface at given intervals of time with an essentially one-dimensional sensor array as the fingerprint surface is moved relative to the sensor array in a direction that is generally perpendicular to the sensor array;
determining which of the plurality of images overlap or partially overlap others of the plurality of images;
disregarding those images which overlap or partially overlap one or more other images; and
constructing a two-dimensional image of the fingerprint surface from only non-overlapping images obtained from said generating step, wherein said measuring is performed simultaneously at each of a plurality of equally spaced measuring points arranged in at least two generally parallel lines spaced apart by a distance different from the distance separating the measuring points, wherein the measuring points of one line are shifted with respect to the measuring points of the next line, and wherein said generating is performed from measurements performed at one of the at least two lines.

2. The method of claim 1, wherein said measuring is performed at each of a plurality of equally spaced measuring points arranged in at least one line corresponding to the essentially one-dimensional sensor array.

3. A method of sensing a fingerprint comprising:
applying a varying voltage to a finger positioned over an electrode;
measuring the capacitance or impedance between the electrode and a capacitive sensor array through a fingerprint surface positioned over both the electrode and the capacitive sensor array, wherein the capacitive sensor array is separately disposed from the electrode and the capacitive sensor array is adapted to detect variations in capacitance or impedance across the array caused by structural features of a portion of the fingerprint surface positioned over the array;
generating a plurality of images of different portions of a fingerprint surface by measuring structural features of the fingerprint surface at given intervals of time with a sensor array as the fingerprint surface is moved relative to the sensor array;
ascertaining the speed of movement of the fingerprint surface relative to the sensor array at each of the given intervals of time by sensing structural features of the fingerprint surface moved over two sensing elements spaced apart by a predetermined distance and determining the speed from the predetermined distance and a time lapse between passage of identical structural features of the fingerprint surface from one of the two sensing elements to the other; and
using the ascertained speed to determine the required relative positioning of at least a portion of the plurality of images to form a two dimensional image of the fingerprint surface larger than any one of the plurality of images.

4. The method of claim 3, further comprising forming a two-dimensional image representative of the structural features of at least a portion of the fingerprint surface using the variations in capacitance or impedance detected in said measuring step.

5. A method for sensing a fingerprint comprising:
generating a plurality of images of different portions of a fingerprint surface by measuring structural features of the fingerprint surface at given intervals of time with a sensor array as the fingerprint surface is moved relative to the sensor array;
ascertaining the speed of movement of the fingerprint surface relative to the sensor array at each of the given intervals of time by sensing structural features of the fingerprint surface moved over two sensing elements spaced apart by a predetermined distance and determining the speed from the predetermined distance and a time lapse between passage of identical structural features of the fingerprint surface from one of the two sensing elements to the other; and
using the ascertained speed to determine the required relative positioning of at least a portion of the plurality of images to form a two dimensional image of the fingerprint surface larger than any one of the plurality of images.

6. The method of claim 5, wherein one of the two sensing elements comprises a sensor in the sensor array.

7. The method of claim 5, wherein each of the two sensing elements is disposed in a different one of two groups of sensing elements arranged in two spaced-apart, generally parallel lines of sensing elements.

8. A method for sensing a fingerprint comprising:
applying a varying voltage to a finger positioned over an electrode;
measuring the capacitance or impedance between the electrode and an essentially one-dimensional capacitive sensor array through a fingerprint surface positioned over both the electrode and the capacitive sensor array, wherein the capacitive sensor array is separately disposed from the electrode and the array of capacitive sensors is adapted to detect variations in capacitance or impedance across the array caused by structural features of a portion of the fingerprint surface positioned over the array;
generating a plurality of images of different portions of a fingerprint surface by measuring structural features of the fingerprint surface at given intervals of time with the capacitive sensor array as the fingerprint surface is moved relative to the sensor array in a direction that is generally perpendicular to the sensor array;
ascertaining the speed of movement of the fingerprint surface relative to the sensor array by sensing structural features of the fingerprint surface moved over two sensing elements spaced apart by a predetermined distance and determining the speed from the predetermined distance and a time lapse between passage of identical structural features of the fingerprint surface over the two sensing elements;
using the ascertained speed to determine which of the plurality of images overlap or partially overlap others of the plurality of images;
disregarding those images which overlap or partially overlap one or more other images; and
constructing a two-dimensional image of the fingerprint surface from only non-overlapping images obtained from said generating step.

9. An apparatus for sensing a fingerprint comprising:
an essentially one-dimensional sensor array and associated circuitry constructed and arranged to generate a plurality of images of different portions of a fingerprint surface by measuring structural features of the fingerprint surface at given intervals of time as the fingerprint surface is moved relative to said sensor array in a direction that is generally perpendicular to said sensor array;

at least one pair of sensing elements, where the sensing elements in each pair are spaced apart by a predetermined distance and are constructed and arranged to sense structural features of the fingerprint surface moved over said two sensing elements of each pair, to determine a time lapse between passage of identical structural features over one sensing element and then the other, and to determine the speed of movement of the fingerprint surface relative to the sensor array from the predetermined distance and the time lapse;

means for determining which of the plurality of images overlap or partially overlap others of the plurality of images from the speed determined by said two sensing elements and to disregard those images which overlap or partially overlap one or more other images; and means for constructing a two-dimensional image of the fingerprint surface from only non-overlapping images generated by said sensor array.

10. The apparatus of claim 9, further comprising an electrode and associated circuitry constructed and arranged to apply a varying voltage to a finger positioned over said electrode, wherein said sensor array is separately disposed from said electrode, and wherein said sensor array is a constructed and arranged to measure the capacitance or impedance between said electrode and said sensor array through a fingerprint surface positioned over both said electrode and said sensor array and to detect variations in capacitance or impedance across said array caused by structural features of a portion of the fingerprint surface positioned over said array.

11. The apparatus of claim 9, wherein one of the two sensing elements of each pair comprises a sensor in the sensor array.

12. The apparatus of claim 9, wherein each of the two sensing elements of each pair is disposed in a different one of two groups of sensing elements arranged in two spaced-apart, generally parallel lines of sensing elements.

* * * * *